(12) United States Patent
Woods et al.

(10) Patent No.: US 8,888,014 B2
(45) Date of Patent: Nov. 18, 2014

(54) TASSEL ASSEMBLY INCLUDING A FRAGRANCE DELIVERY ARRANGEMENT

(75) Inventors: Steven Woods, Medina, OH (US); Rebecca Mengay, Medina, OH (US)

(73) Assignee: The A. I. Root Company, Medina, OH (US)

( * ) Notice: Subject to any disclaimer, the term of this patent is extended or adjusted under 35 U.S.C. 154(b) by 467 days.

(21) Appl. No.: 13/263,214

(22) PCT Filed: Apr. 6, 2010

(86) PCT No.: PCT/US2010/030065
§ 371 (c)(1),
(2), (4) Date: Mar. 26, 2012

(87) PCT Pub. No.: WO2010/118000
PCT Pub. Date: Oct. 14, 2010

(65) Prior Publication Data
US 2012/0168529 A1    Jul. 5, 2012

Related U.S. Application Data

(60) Provisional application No. 61/166,959, filed on Apr. 6, 2009.

(51) Int. Cl.
*A61L 9/12*        (2006.01)
*A61L 9/04*        (2006.01)
*D04D 7/08*        (2006.01)

(52) U.S. Cl.
CPC .......................................... *A61L 9/12* (2013.01)
USPC .................. 239/60; 239/57; 239/289; 28/147

(58) Field of Classification Search
USPC ................. 239/6, 34, 36, 53–56, 60, 289, 57; 28/147; 16/442; 2/244; 428/28, 99, 428/100; 24/715.5, 716
See application file for complete search history.

(56) References Cited

U.S. PATENT DOCUMENTS

| | | | |
|---|---|---|---|
| 1,582,866 A | 4/1926 | Callowhill | |
| 1,820,328 A * | 8/1931 | Schlegel | 16/442 |
| 1,896,060 A | 1/1933 | Colby | |
| 1,983,496 A | 12/1934 | Ganz | |
| 4,200,229 A * | 4/1980 | Spector | 239/57 |
| 4,708,851 A | 11/1987 | Freytag Von Loringhoven | |
| 6,066,371 A | 5/2000 | Zehetner | |
| 7,125,187 B2 | 10/2006 | Osti | |

OTHER PUBLICATIONS

International Search Report mailed May 18, 2010 for International application No. PCT/US10/30065.
Written Opinion mailed May 18, 2010 for International application No. PCT/US10/30065.

* cited by examiner

*Primary Examiner* — Darren W Gorman
(74) *Attorney, Agent, or Firm* — Fay Sharpe LLP

(57) ABSTRACT

A fragrance delivery system similar in appearance, or used in similar locations as a tassel assembly having a fragrance delivery arrangement is provided. The fragrance delivery system similar in appearance, or used in similar locations as a tassel includes an attachment component for hanging the fragrance delivery system similar in appearance, or used in similar locations a tassel, from a conventional supporting article, a head component having a decorative configuration and a skirt component connected to the head component. The skirt component includes a support member and may or may not include a skirt of various materials including strings, cloth, ribbons, wood, glass, plastic or other decorative elements suspended from the support member. A fragrance delivery arrangement is releasably connected to the head component and may or may not be at least partially concealed by the skirt.

2 Claims, 2 Drawing Sheets

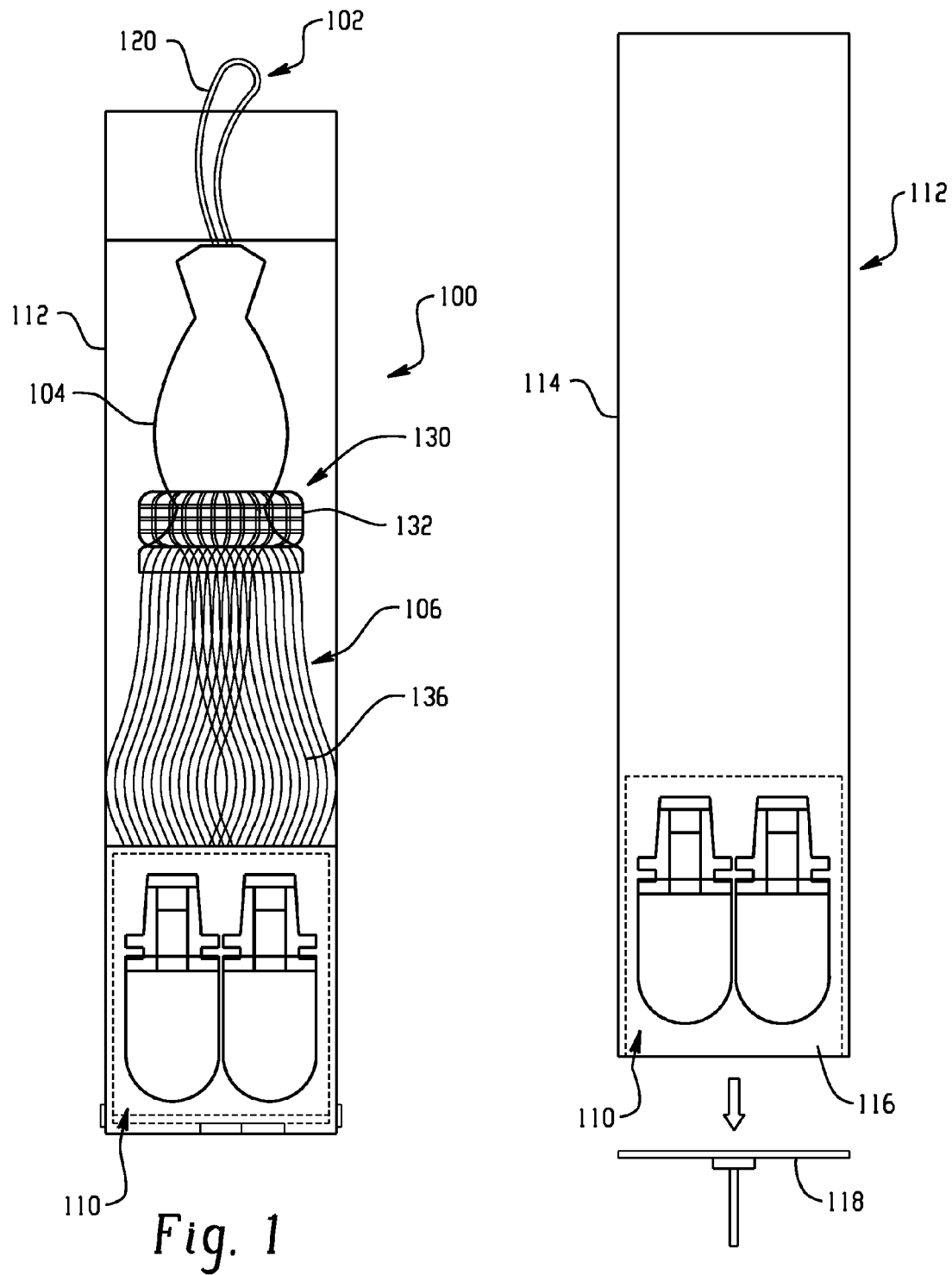

TASSEL ASSEMBLY INCLUDING A FRAGRANCE DELIVERY ARRANGEMENT

CROSS REFERENCE TO RELATED APPLICATIONS

The present application claims priority from U.S. Provisional Patent Application Ser. No. 61/166,959 filed 6 Apr. 2009, which provisional patent application is expressly incorporated herein by reference, in its entirety.

BACKGROUND

The present disclosure relates generally to a fragrance delivery arrangement and, more particularly, to a decorative fragrance delivery assembly or system similar in appearance, or used in similar locations as a tassel, having a fragrance delivery arrangement releasably connected thereto.

Tassels are used in a wide variety of decorative applications. Hanging tassels typically employ a loop that is used to suspend the tassel from a supporting article, such as a chair, lamp, curtain rod, etc. Other types of tassels employ a pair of loops, which enable the tassel to be hung on a hook or a bracket and employed as a curtain tie-back. Conventional tassels normally employ three primary components: a cord component, a decorative head component and a skirt component that hangs from the head component. These components are typically permanently interconnected, which allow for little flexibility associated with the design and use of the tassel. Accordingly, the present disclosure provides an improved design of a fragrance delivery system similar in appearance, or used in similar locations as a tassel which includes a fragrance delivery arrangement.

BRIEF DESCRIPTION

In accordance with one aspect, a decorative fragrance delivery system similar in appearance, or used in similar locations as a tassel having a fragrance delivery arrangement is provided. The tassel assembly comprises an attachment component for hanging the fragrance delivery system from a conventional supporting article, a head component having a decorative configuration and a skirt component connected to the head component. The skirt component includes a support member and may or may not include a skirt of various materials including strings, cloth, ribbons, wood, glass, plastic or other decorative elements suspended from the support member. A fragrance delivery arrangement is releasably connected to the head component and may be at least partially concealed by any skirting material.

In accordance with another aspect, the fragrance delivery system comprises an attachment component for hanging the fragrance delivery system from an associated supporting article, a head component, and may or may not include a skirt of various materials connected to the head component. A replaceable fragrance delivery arrangement may be at least partially concealed by the skirt component. The fragrance delivery arrangement includes an attachment member releasably connected to the head component and a fragrance emitting element releasably connected to the attachment member for holding therein a fragrance emitting substance.

In accordance with yet another aspect, the fragrance delivery system comprises an attachment component for hanging the fragrance delivery system assembly from an associated supporting article, a head component, and a skirt connected to the head component. A replaceable fragrance delivery arrangement is releasably connected to the head component and may or may not be at least partially concealed by the skirt component. The fragrance delivery arrangement includes an attachment member and a fragrance emitting element releasably connected to the attachment member. The fragrance emitting element will attach to the head component or skirt with any releasable method, including, but not limited to a friction fit assembly comprised of a bore in the head component which receives a tapered fragranced element, clip, Velcro, adhesive, tape, hook, or tie.

BRIEF DESCRIPTION OF THE DRAWINGS

FIGS. 1 and 2 are schematic illustrations of the decorative tassel assembly according to the present disclosure packaged for retail sale.

DETAILED DESCRIPTION

Figure 6:
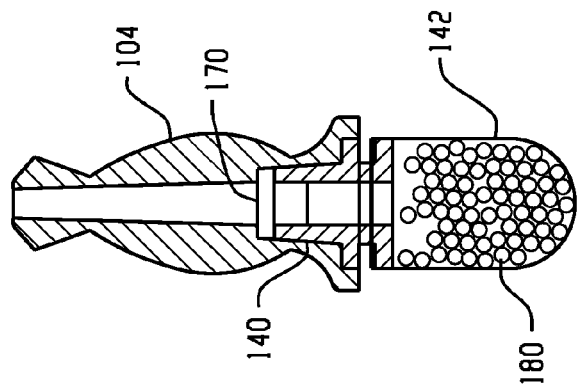
FIGS. 3-6 are partial exploded assembly views of the decorative tassel assembly of FIG. 1 including a fragrance delivery arrangement.
Figure 5:
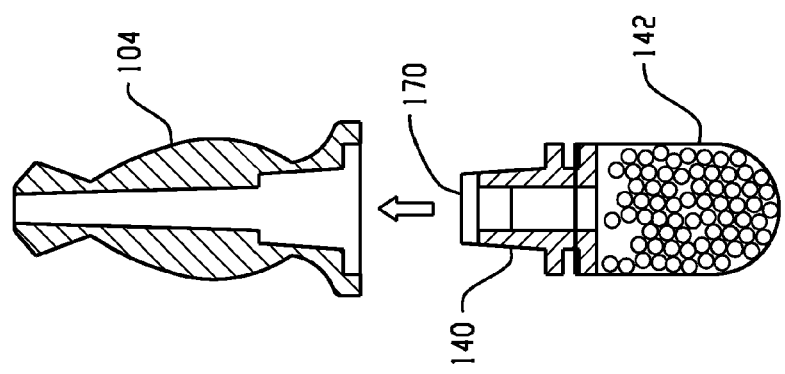
Figure 4:
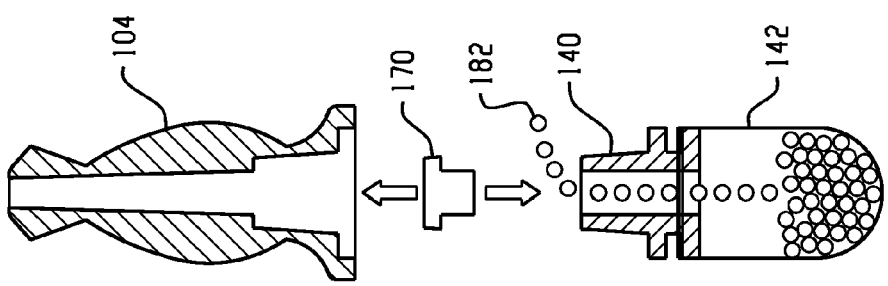

Referring now to the drawings wherein the showings are for purpose of illustrating one or more embodiments only and not for purposes of limiting the same, FIGS. 1 and 2 illustrate a decorative fragrance delivery system similar in appearance, or used in similar locations as a tassel 100 packaged for retail according to one exemplary embodiment of the present disclosure. The fragrance delivery system 100 is typically used for decorative purposes in a manner that is well known. For example, the fragrance delivery system 100 can be hung from a conventional supporting article, such as a curtain rod. The fragrance delivery system 100 may also be hung from a wide variety of other articles, such as chairs, lamps, fans, etc. in a known manner or employed as a curtain tie-back, for example. However, these enumerated articles and uses should not be construed as limiting the present disclosure.

As shown in FIG. 1, the fragrance delivery system 100 includes an upper attachment component 102, an intermediate head component 104 and a lower skirt 106. As will be discussed in greater detail below, a replaceable fragrance delivery arrangement 110 is releasably connected to the head component 104. The fragrance delivery system 100 can be packaged in the depicted exemplary packaging arrangement for retail sale. The packaging arrangement comprises a generally rectangular package or box 112 preferably having a first compartment 114 and a separate second compartment 116 (FIG. 2). A wall 117 divides the first compartment from the second compartment. The first compartment 114 is configured to hold therein the attachment component 102, head component 104 and skirt 106 in an assembled condition. According to one aspect of the packaging arrangement, the tassel assembly is hung by the upper attachment component 102 within the first compartment 114. The second compartment 116 may be configured to hold therein at least one fragrance delivery arrangement 110. As shown, two fragrance delivery arrangements are held in the second compartment 116, although it is contemplated the only one fragrance delivery arrangement is used at a time. A separate end cap 118 can be provided to close an open end of the second compartment of the box. This allows for separate storage of the fragrance delivery arrangement 110 within the box 112. It should be appreciated that alternative retail packaging arrangements for the fragrance delivery system 100 are contemplated and may be used without departing from the scope and intent of the present disclosure. For example, a first package may be used for retail of the component 102, head component 104 and skirt 106, and a second package used for the fragrance delivery arrangement.

The attachment component 102 may comprise, but is not limited to a fibrous natural or synthetic rope material, ribbon, plastic, metal, wood, wire, or a fastenable clip. In the depicted exemplary embodiment, the fastenable component includes a single loop 120 which can be configured to hang the fragrance delivery system 100 from the conventional supporting article. In alternative embodiments, more than one loop may be used so that the fragrance delivery system 100 can serve as a curtain tie-back. In still other embodiments, the attachment component 102 can be omitted altogether. The presence and number of loops of the attachment component 102 are determined by the particular hanging application or end use for which the fragrance delivery system 100 is intended.

The head component 104 can include a decorative shape or configuration. For example, in the depicted exemplary embodiment, the head component 104 is generally pear shaped. In alternative embodiments, the head component may feature a wide variety of other arbitrary, natural and/or aesthetic shapes. The decorative shapes may be selected as for example appropriate for various holiday seasons and celebrations. The head component 104 can be composed of a wide variety of materials including wood, synthetics, ceramics, as well as various combinations of such materials. In some cases, a leather or fabric covering may be applied over an underlying form. The particular shapes and materials of construction of the head component 104 are not germane to the present disclosure.

Figure 3:
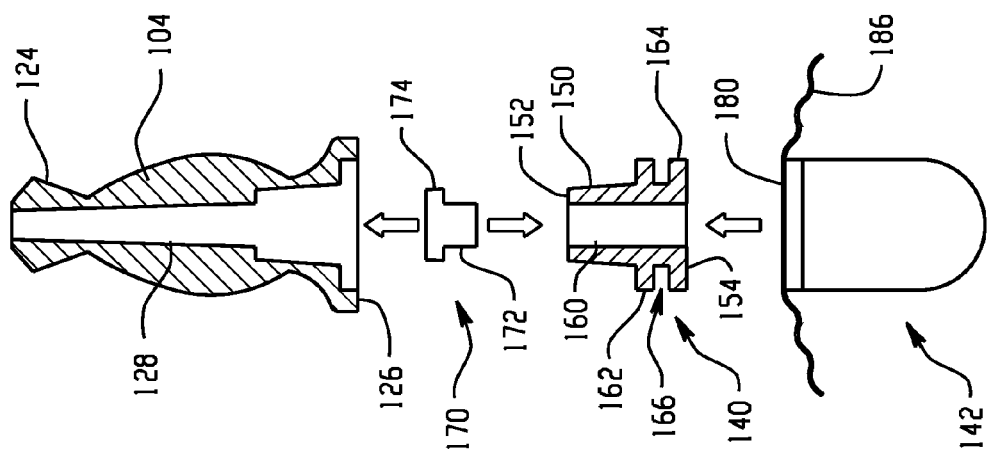

With additional reference to FIG. 3, the head component 104 generally includes a first or upper end 124 and a second or lower end 126. A bore or opening 128 extends longitudinally between the first and second ends; although, this is not required. For example, instead of the bore 128 extending longitudinally between the first and second ends of the head component, the bore (or a recess) 128 may be located at the second end 126 of the head component 104. As shown, the bore 128 defines an axis which is coincident with a longitudinal axis of the head component 104. As will be discussed in greater detail below, the bore 128 may be configured to at least partially receive therein the fragrance delivery arrangement 110.

The skirt 106 can include an underlying support member 130 which is configured to be releasably secured to the second end 126 of the head component 104. The support member can be formed from a variety of materials, such as wood, plastic or ceramic materials. A skirt 132, which may be fringed material, wraps around and is secured to the support member 130. Adhesive is used in a preferred embodiment to secure the skirt 132 to the support member 130. Skirting material which may include, but is not limited to, cloth, ribbons, wood, glass, plastic or other decorative elements 136 is attached to and depend from the skirt 132. In this manner, the skirt is suspended from the support member 130.

As indicated previously, the attachment component 102 and the skirt 106 are attached to the head component, and preferably attached to respective first and second ends 124 and 126 of the head component 104. An attachment component anchoring device (not shown) can be carried by the attachment component 102 and may be configured to fit within the bore 128 of the head component 104. The support member 130 of the skirt 106 is configured to fit around the second end 126 of the head component 104.

With reference now to FIGS. 3-6, assembly of the replaceable fragrance delivery arrangement 110 to the head component 104 is illustrated. In the depicted exemplary embodiment, the fragrance delivery arrangement 110 generally includes an attachment member 140 and a fragrance emitting element 142 which is releasably connected to the attachment member 140. The attachment member includes a body 150 having a first end portion 152 and a second end portion 154. As shown, the body 150 is generally cylindrically shaped, the first end portion 152 being angled convergently towards a longitudinal axis of the body 150; although, alternative shapes for the body are contemplated. A bore 160 extends longitudinally between the first and second end portions of the body 150. In the assembled condition, an axis of the bore 160 is coincident with the axis of the bore 128 of the head component 104. The attachment member 140 further includes a first flange 162 and a second flange 164 which is spaced from the first flange to define a groove 166 therebetween. Each of the first and second flanges extends radially from the body 150. The second flange 164 is located adjacent the second end portion 154 of the body 150. A cap 170 is provided for closing the bore 160 at the first end portion 152 of the attachment member 140. The cap 170 is generally T-shaped in cross-section and includes a cylindrical part 172 which is dimensioned to be received within the bore 160 and an upper part 174. Once secured within the bore, a side surface of the upper part 174 is contiguous with a side surface of the body 150. Alternatively, the shoulder 174 may be omitted and the cap comprised as a simpler, cylindrical component 172. As shown, the cap 170 is separate from the attachment member 140, although, it should be appreciated that the cap can be integrally formed with or connected to the attachment member.

The breathable member 142 is formed in the shape of a bag or pouch and includes an open end 180 for receiving therein a fragrance emitting member, such as scented beads 182. The breathable member is preferably fabricated from a single piece of breathable material which allows the fragrance from the scented beads to exude from the material. In the depicted exemplary embodiment, the breathable member 142 includes a fastening mechanism such as a pair of ties 186 located at the open end 180 to releasably attach the breathable member 142 to the attachment member 140. Particularly, the breathable member 142 is positioned around the second flange 164 such that the open end 180 is located in the groove 166. The ties 186 are then tied to each other within the groove. It should be appreciated that alternative manners for connecting the breathable member 142 to the attachment member 140 are contemplated. For example, the open end 180 can include an elastic band, zip tie, wire, or other method of attachment which can be secured within the groove 166 of the attachment member.

To assemble the fragrance delivery arrangement 110, the breathable member 142 is secured to the attachment member 140 by tying the ties 186 within the groove 166. Scented beads 182 are then poured into the breathable member 142. Particularly, the open end 180 of the breathable member is in communication with the bore 160 of the attachment member. The scented beads are poured into the bore 166 at the first end portion 152, the scented bead dropping into the breathable member 142. Once the breathable member 142 is filled to a desired level with the scented beads 182, the cap 170 is secured to the first end portion 152 of the attachment member 140. The cap 170 is subsequently inserted into end portion 152 and closes the opening of the central bore 160 such that the scented beads cannot escape the breathable member 142. The head component 104 is configured to at least partially receive the attachment member 140. Particularly, the attachment member 140 is at least partially fitted within the bore 128 of the head component 104. As shown, a lower portion of the bore 128 of the head component 104 is shaped to releasably receive the first end portion 152 and the first radial flange 162 of the body 150 of the attachment member 140. Once secured within the bore 128, such as by press-fitting the attachment member 140 into the bore 128, the fragrance delivery arrangement 110 is at least partially concealed by the skirt plurality of tassel strands 136 of the tassel component 106. The scented beads 182 can easily be changed or refilled by simply removing the attachment member 140 from the head component 104, removing the cap 170 and then removing the scented beads from the breathable member 142 or refilling the breathable member with new scented beads. Alternatively, it should be appreciated that instead of replacing the scented beads, a separate fragrance emitting element can be releasably connected to the head component 104.

It will be appreciated that various ones of the above-disclosed and other features and functions, or alternatives thereof, may be desirably combined into many other different systems or applications. Also various presently unforeseen or unanticipated alternatives, modifications, variations or improvements therein may be subsequently made by those skilled in the art which are also intended to be encompassed by the following claims.

The invention claimed is:

1. A fragrance delivery tassel system comprising:

an attachment component for hanging the tassel assembly from an associated supporting article;

a head component including a bore;

a tassel component connected to the head component; and a replaceable fragrance delivery arrangement releasably connected to the head component and at least partially concealed by the tassel component, the fragrance delivery arrangement including:

an attachment member releasably secured to the head component for selective attachment and detachment thereto;

a fragrance emitting element received in a breathable member that is releasably connected to the attachment member, the breathable member allowing fragrance from the fragrance emitting member to exude therefrom.

2. The fragrance delivery system of claim 1, further including a cap configured to close a bore of the attachment member.

\* \* \* \* \*